US009193706B2

(12) United States Patent
Umetani et al.

(10) Patent No.: US 9,193,706 B2
(45) Date of Patent: Nov. 24, 2015

(54) METHOD FOR PRODUCING 3,4-DIHYDROISOQUINOLINE DERIVATIVES AND PRODUCTION INTERMEDIATES OF SAME

(71) Applicant: MITSUI CHEMICALS AGRO, INC., Minato-ku (JP)

(72) Inventors: Hideki Umetani, Yasu (JP); Nobuhiro Kondo, Mobara (JP); Fumie Kajino, Yasu (JP); Munetsugu Morimoto, Yasu (JP)

(73) Assignee: MITSUI CHEMICALS AGRO, INC., Tokyo (JP)

( * ) Notice: Subject to any disclaimer, the term of this patent is extended or adjusted under 35 U.S.C. 154(b) by 0 days.

(21) Appl. No.: 14/347,426

(22) PCT Filed: Sep. 28, 2012

(86) PCT No.: PCT/JP2012/075085
§ 371 (c)(1),
(2) Date: Mar. 26, 2014

(87) PCT Pub. No.: WO2013/047750
PCT Pub. Date: Apr. 4, 2013

(65) Prior Publication Data
US 2014/0228576 A1 Aug. 14, 2014

(30) Foreign Application Priority Data
Sep. 29, 2011 (JP) ................. 2011-213688

(51) Int. Cl.
*C07D 401/04* (2006.01)
*C07D 217/02* (2006.01)
*C07D 217/16* (2006.01)

(52) U.S. Cl.
CPC ............ *C07D 401/04* (2013.01); *C07D 217/02* (2013.01); *C07D 217/16* (2013.01)

(58) Field of Classification Search
None
See application file for complete search history.

(56) References Cited

U.S. PATENT DOCUMENTS

| 5,442,065 A | 8/1995 | Magnus et al. |
| 2008/0275242 A1 | 11/2008 | Ito et al. |
| 2010/0204234 A1 | 8/2010 | Hartmann et al. |
| 2012/0282349 A1 | 11/2012 | Tamagawa et al. |

FOREIGN PATENT DOCUMENTS

| WO | WO 2004/013094 A2 | 2/2004 |
| WO | WO 2005/070917 A1 | 8/2005 |
| WO | WO 2007/011022 A1 | 1/2007 |
| WO | WO 2007/100758 A2 | 9/2007 |
| WO | WO 2008/116920 A2 | 10/2008 |
| WO | WO 2011/077514 A1 | 6/2011 |

OTHER PUBLICATIONS

International Search Report (PCT/ISA/210) mailed on Nov. 27, 2012, by the Japanese Patent Office as the International Searching Authority for International Application No. PCT/JP2012/075085.
Jain et al., "Synthesis of Benzoxazolyl-1,4-diazepine, 1,5-Benzodiazepine & Other Heterocycles", Indian Journal of Chemistry, 1975, pp. 304-305, vol. 13, No. 3, Chart 1.
Naik et al., "Studies in the Vilsmeier-Haack Reaction: Part XVI—Synthesis of 7-Amino-3-hetrarylquinoline Fluorophore & Derivatives", Indian Journal of Chemistry, Section B: Organic Chemistry Including Medicinal Chemistry, 1977, pp. 506-508, vol. 15B, No. 6.
Nair et al., "Synthesis and fluorescence properties of 3-benzoxa- and thiazol-2-ylquinoline-5 or 7-maleimides", Indian Journal of Chemistry, Section B: Organic Chemistry Including Medicinal Chemistry, 2004, pp. 1944-1949, vol. 43B, No. 9.
Kurti et al., Strategic Applications of Named Reactions in Organic Synthesis, 2005, pp. 468-469.
International Search Report (Forms PCT/ISA/373 and PCT/ISA/237) dated Apr. 1, 2014, by the International Bureau of WIPO as the International Searching Authority for International Application No. PCT/JP2012/075085.
Gilan et al., "Organometallic Derivatives of Carbazole and Quinoline. Amides of 3-Quinoline-carboxylic Acid", Journal American Chemistry Society, Jun. 1941, pp. 1553-1556, vol. 63.
Tanaka et al., "Reactions of 2 Formyl-3-methoxypropionitrile Derivatives as Electrophilic Reagent", Chemistry Pharm. Bull, 1978, pp. 1558-1569, vol. 26, No. 5.
Hamana et al., "Studies on Tertiary Amine Oxides. LXIV. Reaction of 4-Nitroquinoline 1-Oxide and Related Compounds with Potassium Cyanide", Chemistry Pharm. Bull, 1978, pp. 3856-3862, vol. 26, No. 12.
Charpentier et al., An Efficient Synthesis of 3-Cyanoquinoline Derivatives, Tetrahedron Letters 39 (1998), pp. 4013-4016.
Kuppuswamy Nagarajan et al.: "Vilsmeier-Haack Reaction of 1-Methyl-3, 4-Dihydroisoquinolines—Unexpected Formation of 2, 3-Bisdimethylamino-5, 6-Dihydropyrrolo [2,1-a]Isonquinolines," Tetrahedron Letters, vol. 33, No. 47, pp. 7229-7232, 1992.
Extended Search Report issued by the European Patent Office in corresponding European Patent Application No. 12835210 on Apr. 21, 2015 (7 pages).

*Primary Examiner* — Zinna Northington Davis
(74) *Attorney, Agent, or Firm* — Buchanan, Ingersoll & Rooney PC

(57) ABSTRACT

Provided are an efficient method for producing 3,4-dihydroisoquinoline derivatives and useful production intermediates thereof. Provided is a method for producing 3,4-dihydroisoquinoline derivatives represented by general formula (1), comprising converting a compound represented by general formula (3) in the presence of acid after reacting with an aniline derivative, or converting a compound represented by general formula (3) by reacting with an aniline derivative in the presence of an acid.

21 Claims, No Drawings

METHOD FOR PRODUCING 3,4-DIHYDROISOQUINOLINE DERIVATIVES AND PRODUCTION INTERMEDIATES OF SAME

TECHNICAL FIELD

The present invention relates to a method for producing 3,4-dihydroisoquinoline derivatives and production intermediates thereof.

BACKGROUND ART

Numerous chemicals have been proposed for the purpose of controlling diseases in agricultural and horticultural crops. For example, a 3,4-dihydroisoquinoline derivative represented by general formula (1):

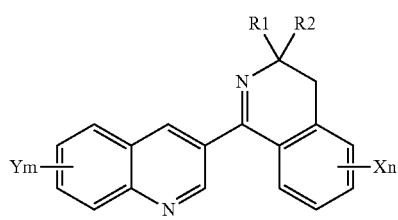

wherein R1 and R2 independently represent an optionally substituted alkyl group having 1 to 6 carbon atoms or R1 and R2 together with the carbon atom to which they are bound form an optionally substituted cycloalkyl group having 3 to 10 carbon atoms, X represents a halogen atom, optionally substituted alkyl group having 1 to 6 carbon atoms or optionally substituted alkoxy group having 1 to 6 carbon atoms, n represents an integer of 0 to 4, Y represents a halogen atom, optionally substituted alkyl group having 1 to 6 carbon atoms or optionally substituted alkoxy group having 1 to 6 carbon atoms, and m represents an integer of 0 to 4, is disclosed in Patent Document 1 as being useful as an agricultural and horticultural microbicide. Moreover, a group of compounds derived from a compound represented by general formula (1) are also effective as agricultural and horticultural microbicides, and these compounds can also be intermediates for the production of agricultural and horticultural microbicides (Patent Document Nos. 1 and 2). Consequently, being able to produce these compounds both simply and efficiently is an extremely important issue.

According to Patent Document 1, a compound represented by general formula (1) is disclosed as being able to be prepared by using a 3-cyanoquinoline derivative as a starting material and reacting with a phenethyl alcohol derivative or styrene derivative, thus demonstrating that a 3-cyanoquinoline derivative is an important raw material.

An examination of the prior art relating to 3-cyanoquinoline reveals that it is produced by methods such as: (I) a method in which 3-bromoquinoline and copper cyanide are reacted at 250° C. (Non-Patent Document 1), (II) a method in which 2-dimethoxymethylacrylonitrile and aniline are reacted followed by converting with aluminum chloride (Non-Patent Document 2), (III) a method in which 4-nitroquinoline-1-oxide and potassium cyanide are reacted followed by chlorinating with phosphorous oxychloride and further subjecting to catalytic hydrogenation using palladium as catalyst (Non-Patent Document 3) for conversion, (IV) a method in which 3-bromoquinoline, sodium cyanide, potassium iodide, copper iodide and dimethyl ethylenediamine are reacted for 24 hours in toluene for conversion (Patent Document 3), and (V) a method in which aniline and a sodium salt of 3,3-dimethoxy-2-formyl propionitrile are reacted in the presence of hydrochloric acid followed by converting to a substituted cyanoquinoline with p-toluenesulfonic acid (Non-Patent Document 4).

However, these methods have the problems indicated below. In the method of (I), in addition to requiring an extremely high reaction temperature of 250° C., copper cyanide is used, which is highly toxic and causes problems on disposal. In the method of (II), the total yield is only about 4%, thus indicating poor productivity. In the method of (III), in addition to using highly toxic potassium cyanide, catalytic hydrogenation using an expensive palladium catalyst only demonstrates a yield of about 56%. In the method of (IV), in addition to using transition metals that present problems on disposal and highly toxic sodium cyanide, the reaction time is long resulting in it being not an efficient method. In the method of (V), although the method per se is superior, the substituents on aniline are limited to strong electron donating groups such as a methoxy group. On the other hand, the reaction does not proceed not only in the case of aniline substituted with a fluorine atom or methyl group, but also in the case of unsubstituted aniline, thereby indicating that this method lacks versatility.

As can be understood from the above, since conventional production methods using 3-cyanoquinoline derivatives as starting materials have problems with respect to productivity of the 3-cyanoquinoline per se as well as only allowing the acquisition of 3-cyanoquinoline having a limited range of substituents, there has been a fervent desire for a method for efficiently producing 3,4-dihydroisoquinoline derivatives as an alternative to these methods.

PRIOR ART DOCUMENTS

Patent Documents

Patent Document 1: International Publication No. WO 2005/70917
Patent Document 2: International Publication No. WO 2011/77514
Patent Document 3: International Publication No. WO 2004/13094

Non-Patent Documents

Non-Patent Document 1: J. Am. Chem. Soc., Vol. 63, pp. 1553-1556 (1941)
Non-Patent Document 2: Chem. Pharm. Bull., Vol. 26, No. 5, pp. 1558-1569 (1978)
Non-Patent Document 3: Chem. Pharm. Bull., Vol. 26, No. 12, pp. 3856-3862 (1978)
Non-Patent Document 4: Tetrahedron Lett., Vol. 39, pp. 4013-4016 (1998)

DISCLOSURE OF THE INVENTION

Problems to be Solved by the Invention

An object of the present invention is to provide an efficient method for producing 3,4-dihydroisoquinoline derivatives and useful production intermediates thereof.

Means for Solving the Problems

As a result of conducting extensive studies to solve the aforementioned problems, it was found that 3,4-dihydroisoquinoline derivatives can be prepared both simply and efficiently by carrying out a reaction using a novel isoquinolinylidenemalonaldehyde derivative and aniline derivative as starting materials to convert to a novel phenyliminopropanal derivative, followed by cyclizing in the presence of acid. Surprisingly, it became possible to provide various types of 3,4-dihydroisoquinoline derivatives since this method could be carried out in the case of substituted anilines as well. What is even more surprising is that 3,4-dihydroisoquinoline derivatives can be prepared at once by reacting a novel isoquinolinylidenemalonaldehyde derivative and aniline in the presence of acid, thereby providing an effective solution to the aforementioned problems. In addition, by carrying out hydrolysis after having obtained a novel isoquinolinylvinamidinium salt derivative by reacting a 1-methyl-3,4-dihydroisoquinoline derivative with Vilsmeier reagent, it was found that the isoquinolinylidenemalonaldehyde serving as raw material can be prepared efficiently, thereby leading to completion of the present invention.

Namely, the present invention is:

[1] a method for producing a compound represented by general formula (1):

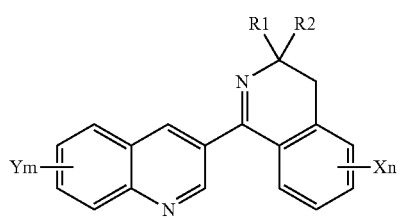

(1)

wherein R1 and R2 independently represent an optionally substituted alkyl group having 1 to 6 carbon atoms or R1 and R2 together with the carbon atom to which they are bound form an optionally substituted cycloalkyl group having 3 to 10 carbon atoms, X represents a halogen atom, optionally substituted alkyl group having 1 to 6 carbon atoms or optionally substituted alkoxy group having 1 to 6 carbon atoms, n represents an integer of 0 to 4, Y represents a halogen atom, optionally substituted alkyl group having 1 to 6 carbon atoms or optionally substituted alkoxy group having 1 to 6 carbon atoms, and m represents an integer of 0 to 4, comprising reacting a compound represented by general formula (2):

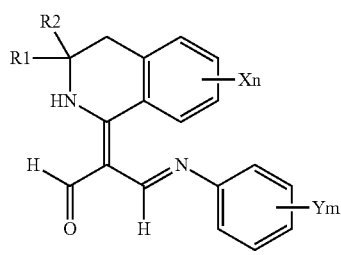

(2)

wherein R1, R2, X, Y, n and m are the same as previously defined, in the presence of an acid;

[2] the method for producing a compound represented by general formula (1) described in [1], wherein R1 and R2 independently represent an optionally substituted alkyl group having 1 to 6 carbon atoms;

[3] the method for producing a compound represented by general formula (1) described in [2], wherein n is 0;

[4] the method for producing a compound represented by general formula (1) described in [1], wherein a compound represented by general formula (2) is obtained by reacting a compound represented by general formula (3):

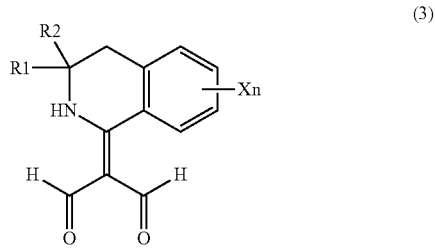

(3)

wherein R1, R2, X and n are the same as in [1], with a compound represented by general formula (4):

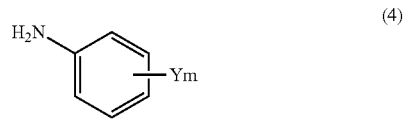

(4)

wherein Y and m are the same as in [1];

[5] the method for producing a compound represented by general formula (1) described in [4], wherein R1 and R2 independently represent an optionally substituted alkyl group having 1 to 6 carbon atoms;

[6] the method for producing a compound represented by general formula (1) described in [5], wherein n is 0;

[7] the method for producing a compound represented by general formula (1) described in [4], wherein a compound represented by general formula (3) is obtained by hydrolyzing a salt containing a compound represented by general formula (5):

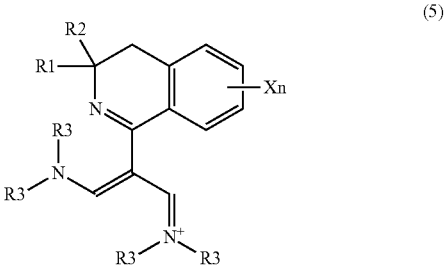

(5)

wherein R1, R2, X and n are the same as in [4] and R3 is an alkyl group having 1 to 3 carbon atoms;

[8] the method for producing a compound represented by general formula (1) described in [7], wherein R1 and R2 independently represent an optionally substituted alkyl group having 1 to 6 carbon atoms;

[9] the method for producing a compound represented by general formula (1) described in [8], wherein n is 0;

[10] the method for producing a compound represented by general formula (1) described in [7], wherein a salt containing a compound represented by general formula (5) is obtained by reacting a compound represented by general formula (6):

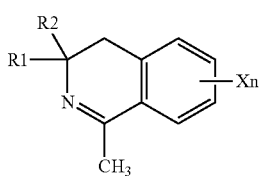

(6)

wherein R1, R2, X and n are the same as in [7], with a salt containing a compound represented by general formula (7):

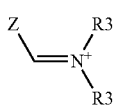

(7)

wherein R3 is the same as in [7] and Z represents a halogen atom;

[11] the method for producing a compound represented by general formula (1) described in [10], wherein R1 and R2 independently represent an optionally substituted alkyl group having 1 to 6 carbon atoms;

[12] the method for producing a compound represented by general formula (1) described in [11], wherein n is 0;

[13] a method for producing a compound represented by general formula (1):

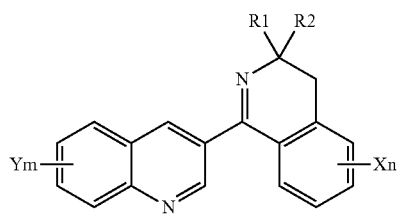

(1)

wherein R1 and R2 independently represent an optionally substituted alkyl group having 1 to 6 carbon atoms or R1 and R2 together with the carbon atom to which they are bound form an optionally substituted cycloalkyl group having 3 to 10 carbon atoms, X represents a halogen atom, optionally substituted alkyl group having 1 to 6 carbon atoms or optionally substituted alkoxy group having 1 to 6 carbon atoms, n represents an integer of 0 to 4, Y represents a halogen atom, optionally substituted alkyl group having 1 to 6 carbon atoms or optionally substituted alkoxy group having 1 to 6 carbon atoms, and m represents an integer of 0 to 4, comprising reacting a compound represented by general formula (3):

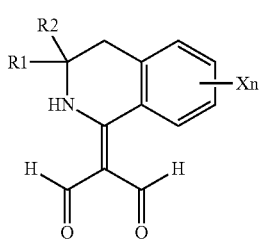

(3)

wherein R1, R2, X and n are the same as previously defined, with a compound represented by general formula (4):

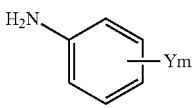

(4)

wherein Y and m are the same as previously defined, in the presence of an acid;

[14] the method for producing a compound represented by general formula (1) described in [13], wherein R1 and R2 independently represent an optionally substituted alkyl group having 1 to 6 carbon atoms;

[15] the method for producing a compound represented by general formula (1) described in [14], wherein n is 0;

[16] the method for producing a compound represented by general formula (1) described in [13], wherein a compound represented by general formula (3) is obtained by hydrolyzing a salt containing a compound represented by general formula (5):

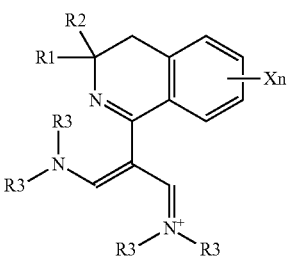

(5)

wherein R1, R2, X and n are the same as in [13] and R3 represents an alkyl group having 1 to 3 carbon atoms;

[17] the method for producing a compound represented by general formula (1) described in [16], wherein R1 and R2 independently represent an optionally substituted alkyl group having 1 to 6 carbon atoms;

[18] the method for producing a compound represented by general formula (1) described in [17], wherein n is 0;

[19] the method for producing a compound represented by general formula (1) described in [16], wherein a salt containing a compound represented by general formula (5) is obtained by reacting a compound represented by general formula (6):

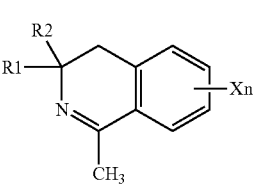

(6)

wherein R1, R2, X and n are the same as in [16], with a salt containing a compound represented by general formula (7):

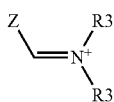

(7)

wherein R3 is the same as in [16] and Z represents a halogen atom;

[20] the method for producing a compound represented by general formula (1) described in [19], wherein R1 and R2 independently represent an optionally substituted alkyl group having 1 to 6 carbon atoms;

[21] the method for producing a compound represented by general formula (1) described in [20], wherein n is 0;

[22] a method for producing a compound represented by general formula (2), comprising reacting a compound represented by general formula (3) with a compound represented by general formula (4) to obtain a compound represented by general formula (2) described in [4];

[23] the method for producing a compound represented by general formula (2) described in [22], wherein R1 and R2 independently represent an optionally substituted alkyl group having 1 to 6 carbon atoms;

[24] the method for producing a compound represented by general formula (2) described in [23], wherein n is 0;

[25] a method for producing a compound represented by general formula (3), comprising hydrolyzing a salt containing a compound represented by general formula (5) to obtain a compound represented by general formula (3) described in [7];

[26] the method for producing a compound represented by general formula (3) described in [25], wherein R1 and R2 independently represent an optionally substituted alkyl group having 1 to 6 carbon atoms;

[27] the method for producing a compound represented by general formula (3) described in [26], wherein n is 0;

[28] a method for producing a salt containing a compound represented by general formula (5), comprising reacting a compound represented by general formula (6) with a salt containing a compound represented by general formula (7) to obtain a salt containing a compound represented by general formula (5) described in [10];

[29] the method for producing a salt containing a compound represented by general formula (5) described in [28], wherein R1 and R2 independently represent an optionally substituted alkyl group having 1 to 6 carbon atoms;

[30] the method for producing a salt containing a compound represented by general formula (5) described in [29], wherein n is 0;

[31] a compound represented by general formula (2) described in [1];

[32] the compound represented by general formula (2) described in [31], wherein R1 and R2 independently represent an optionally substituted alkyl group having 1 to 6 carbon atoms;

[33] the compound represented by general formula (2) described in [32], wherein n is 0;

[34] a compound represented by general formula (3) described in [4];

[35] the compound represented by general formula (3) described in [34], wherein R1 and R2 independently represent an optionally substituted alkyl group having 1 to 6 carbon atoms;

[36] the compound represented by general formula (3) described in [35], wherein n is 0;

[37] a salt containing a compound represented by general formula (5) described in [7];

[38] the salt containing a compound represented by general formula (5) described in [37], wherein R1 and R2 independently represent an optionally substituted alkyl group having 1 to 6 carbon atoms; and,

[39] the salt containing a compound represented by general formula (5) described in [38], wherein n is 0.

Effects of the Invention

According to the present invention, a novel and efficient method for producing 3,4-dihydroisoquinoline derivatives and useful novel production intermediates thereof can be provided. In addition, since a group of target compounds can be prepared efficiently by simple operation, the method of the present invention is also suitable as an industrial manufacturing method.

MODE FOR CARRYING OUT THE INVENTION

The following provides a detailed explanation of embodiments for carrying out the present invention.

An explanation is first provided of compounds represented by general formula (1).

In general formula (1), R1 and R2 are independent and may be the same or different.

The substituents of the optionally substituted alkyl group having 1 to 6 carbon atoms at R1 and R2 in general formula (1) refer to halogen atoms and alkoxy groups having 1 to 6 carbon atoms. The halogen atom is fluorine, chlorine, bromine or iodine. The alkoxy group having 1 to 6 carbon atoms represents a linear or branched alkoxy group such as a methoxy group, ethoxy group, propoxy group, isopropoxy group, butyloxy group, isobutyloxy group, s-butyloxy group, t-butyloxy group, pentoxy group, isopentoxy group, 2-methylbutyloxy group, neopentoxy group, 1-ethylpropoxy group, hexyloxy group, 4-methylpentoxy group, 3-methylpentoxy group, 2-methylpentoxy group, 1-methylpentoxy group, 3,3-dimethylbutyloxy group, 2,2-dimethylbutyloxy group, 1,1-dimethylbutyloxy group, 1,2-dimethylbutyloxy group, 1,3-dimethylbutyloxy group, 2,3-dimethylbutyloxy group or 2-ethylbutyloxy group. It is preferably an alkoxy group having 1 to 4 carbon atoms and more preferably a methoxy group, ethoxy group, propoxy group or isopropoxy group. There are no particular limitations on the number of substituents and each substituent may be the same or different.

The alkyl group in the optionally substituted alkyl group having 1 to 6 carbon atoms at R1 and R2 in general formula (1) represents a linear or branched alkyl group such as a methyl group, ethyl group, propyl group, isopropyl group, butyl group, isobutyl group, s-butyl group, t-butyl group, pentyl group, isopentyl group, 2-methylbutyl group, neopentyl group, 1-ethylpropyl group, hexyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group or 2-ethylbutyl group. It is preferably an alkyl group having 1 to 3 carbon atoms and more preferably a methyl group or ethyl group.

The substituents of the optionally substituted cycloalkyl group having 3 to 10 carbon atoms formed by R1 and R2 together with the carbon atom to which they are bound in general formula (1) have the same meaning as the substituents of the optionally substituted alkyl group having 1 to 6 carbon atoms at R1 and R2 in general formula (1). There are no particular limitations on the number of substituents and each substituent may be the same or different.

The cycloalkyl group in the optionally substituted cycloalkyl group having 3 to 10 carbon atoms formed by R1 and R2 together with the carbon atom to which they are bound in general formula (1) refers to a monocyclic or polycyclic cycloalkyl group having 3 to 10 carbon atoms such as a cyclobutyl group, cyclopentyl group, cyclohexyl group, cycloheptyl group or norbornyl group. It is preferably a cyclobutyl group, cyclopentyl group, cyclohexyl group or cycloheptyl group, and more preferably a cyclopentyl group.

The halogen atom at X in general formula (1) refers to fluorine, chlorine, bromine or iodine.

The optionally substituted alkyl group having 1 to 6 carbon atoms at X in general formula (1) has the same meaning as the optionally substituted alkyl group having 1 to 6 carbon atoms at R1 and R2 in general formula (1).

The substituents of the optionally substituted alkoxy group having 1 to 6 carbon atoms at X in general formula (1) refer to a halogen atom, that is, fluorine, chlorine, bromine or iodine. There are no particular limitations on the number of substituents and each substituent may be the same or different.

The alkoxy group of the optionally substituted alkoxy group having 1 to 6 carbon atoms at X in general formula (1) refers to a linear or branched alkoxy group such as a methoxy group, ethoxy group, propoxy group, isopropoxy group, butyloxy group, isobutyloxy group, s-butyloxy group, t-butyloxy group, pentoxy group, isopentoxy group, 2-methylbutyloxy group, neopentoxy group, 1-ethylpropoxy group, hexyloxy group, 4-methylpentoxy group, 3-methylpentoxy group, 2-methylpentoxy group, 1-methylpentoxy group, 3,3-dimethylbutyloxy group, 2,2-dimethylbutyloxy group, 1,1-dimethylbutyloxy group, 1,2-dimethylbutyloxy group, 1,3-dimethylbutyloxy group, 2,3-dimethylbutyloxy group or 2-ethylbutyloxy group. It is preferably an alkoxy group having 1 to 4 carbon atoms and more preferably a methoxy group, ethoxy group, propoxy group or isopropoxy group.

n in general formula (1) is an integer of 0 to 4.

X may be the same or different when n in general formula (1) is 2 or more.

The halogen atom at Y in general formula (1) has the same meaning as the halogen atom at X in general formula (1).

The optionally substituted alkyl group having 1 to 6 carbon atoms at Y in general formula (1) has the same meaning as the optionally substituted alkyl group having 1 to 6 carbon atoms at X in general formula (1).

The optionally substituted alkoxy group having 1 to 6 carbon atoms at Y in general formula (1) has the same meaning as the optionally substituted alkoxy group having 1 to 6 carbon atoms at X in general formula (1).

m in general formula (1) is an integer of 0 to 4.

Y may be the same or different when m in general formula (1) is 2 or more.

R1, R2, X, Y, n and m in general formula (2) have the same meanings as in general formula (1).

A compound represented by general formula (2) includes the isomers indicated below. These isomers may be present alone or a mixture of two or more types. There are no particular limitations on the mixing ratio in the case of the mixtures.

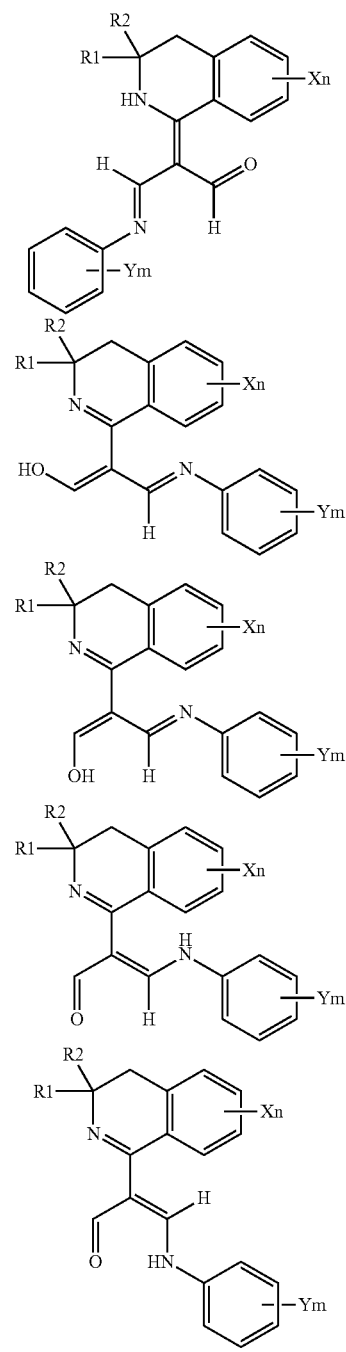

The following provides an explanation of a method for converting from a compound represented by general formula (2) to a compound represented by general formula (1) in the presence of an acid.

The acid used can be an inorganic acid or organic acid, and there are no particular limitations thereon provided it allows the target reaction to proceed. Examples of the inorganic acids include hydrochloric acid, sulfuric acid and phosphoric acid, and the inorganic acid is preferably sulfuric acid or phosphoric acid. Examples of the organic acids include organic carboxylic acids and organic sulfonic acids. Examples of the organic carboxylic acids include trifluoroacetic acid and the like. Examples of the organic sulfonic acids include methanesulfonic acid, trifluoromethanesulfonic acid, benzenesulfonic acid, toluenesulfonic acid, xylenesulfonic acid, chlorobenzenesulfonic acid and naphthalenesulfonic acid. In the case the sulfonic acid has the regioisomers, any isomer is effective.

There are no particular limitations on the amount of acid used provided it is more than 1 equivalent. It is preferably 1 equivalent to 3 equivalents.

Although there are no particular limitations on solvent used in the reaction provided it allows the reaction to proceed, examples thereof include benzene-based solvents such as benzene, toluene, xylene, mesitylene, chlorobenzene or dichlorobenzene, ester-based solvents such as ethyl acetate, isopropyl acetate or butyl acetate, nitrile-based solvents such as acetonitrile, amide-based solvents such as N-methylpyrrolidone, N,N-dimethylformamide or N,N-dimethylacetamide, urea-based solvents such as 1,3-dimethyl-2-imidazolidinone, and chlorine-based solvents such as dichloroethane or chloroform. It is preferably a benzene-based solvent. One type of solvent may be used alone or two or more types can be mixed at an arbitrary ratio.

Although there are no particular limitations on the amount of solvent used provided it allows the reaction to proceed, it is normally 3 times to 50 times the weight of the compound represented by general formula (2).

Although there are no particular limitations on the reaction temperature provided it allows the reaction to proceed, it is normally higher than 40° C. and lower than 200° C. or the boiling point of the solvent.

With respect to moisture present in the reaction, the reaction proceeds efficiently by removing water from the reaction system. At this time, there are no particular limitations on the use of normal pressure or reduced pressure provided the reaction is allowed to proceed. The pressure may be suitably set as necessary.

The following provides a description of a method for post-treatment of the reaction.

A compound represented by general formula (1) forms a salt with acid following completion of the reaction. With regard to the form of the salt, there is one pair of acid or two pairs of acid, or a mixture of one pair and two pairs of acids based on the compound represented by general formula (1). There are no particular limitations on the mixing ratio in the case of the mixtures.

In the case a salt of the compound represented by general formula (1) precipitates, a target substance can be obtained by filtration. In addition, when carrying out a filtration procedure, a solvent can also be added to the reaction mixture. Examples of the solvents used include, but are not limited to, water, ether-based solvents such as diethyl ether, diisopropyl ether or methyl t-butyl ether, alcohol-based solvents such as methanol, ethanol or isopropanol, benzene-based solvents such as benzene, toluene, xylene, mesitylene, chlorobenzene or dichlorobenzene, ester-based solvents such as ethyl acetate, isopropyl acetate or butyl acetate, nitrile-based solvents such as acetonitrile, hydrocarbon-based solvents such as hexane, heptane, cyclohexane or methylcyclohexane, and halogen-based solvents such as dichloromethane, dichloroethane or chloroform.

The salt of a compound represented by general formula (1) obtained in this manner can be subjected to washing, re-precipitation or recrystallization with a suitable solvent as necessary. Although there are no particular limitations on the solvent used provided it allows the target procedure to be carried out, examples thereof include water, ether-based solvents such as diethyl ether, diisopropyl ether or methyl t-butyl ether, alcohol-based solvents such as methanol, ethanol or isopropanol, benzene-based solvents such as benzene, toluene, xylene, mesitylene, chlorobenzene or dichlorobenzene, ester-based solvents such as ethyl acetate, isopropyl acetate or butyl acetate, nitrile-based solvents such as acetonitrile, hydrocarbon-based solvents such as hexane, heptane, cyclohexane or methylcyclohexane, and halogen-based solvents such as dichloromethane, dichloroethane or chloroform. In addition, one type of these solvents can be used alone or two or more types can be used by mixing at an arbitrary ratio.

The salt of a compound represented by general formula (1) can also be converted to a free compound represented by general formula (1) with an aqueous alkaline solution. The aqueous alkaline solution used is that in which, for example, sodium hydroxide, potassium hydroxide, sodium bicarbonate, potassium bicarbonate, sodium carbonate, potassium carbonate or ammonia or the like, is dissolved in water. At this time, a solvent can be added, examples of which include water, ether-based solvents such as diethyl ether, diisopropyl ether or methyl t-butyl ether, alcohol-based solvents such as methanol, ethanol or isopropanol, benzene-based solvents such as benzene, toluene, xylene, mesitylene, chlorobenzene or dichlorobenzene, ester-based solvents such as ethyl acetate, isopropyl acetate or butyl acetate, hydrocarbon-based solvents such as hexane, heptane, cyclohexane or methylcyclohexane, and halogen-based solvents such as dichloromethane, dichloroethane or chloroform. One type of these solvents can be used alone or two or more types can be used by mixing at an arbitrary ratio. In addition, if a state after desalting allows liquid separation, liquid separation can be directly carried out. There are no particular limitations on the number of liquid separation procedures. The target compound represented by general formula (1) can be obtained by distilling off the solvent following liquid separation. Although moisture can be removed with a desiccant such as sodium sulfate or magnesium sulfate before distilling off the solvent, this operation is not essential. In addition, a free compound represented by general formula (1) can be filtered out in the case the compound precipitates.

The free compound represented by general formula (1) obtained in this manner can be further purified by washing, re-precipitating or recrystallizing with a suitable solvent. Examples of the solvents used include water, ether-based solvents such as diethyl ether, diisopropyl ether or methyl t-butyl ether, alcohol-based solvents such as methanol, ethanol or isopropanol, benzene-based solvents such as benzene, toluene, xylene, mesitylene, chlorobenzene or dichlorobenzene, ester-based solvents such as ethyl acetate, isopropyl acetate or butyl acetate, hydrocarbon-based solvents such as hexane, heptane, cyclohexane or methylcyclohexane, and halogen-based solvents such as dichloromethane, dichloroethane or chloroform, and one type of these solvents can be used alone or two or more types can be used by mixing at an arbitrary ratio. In addition, the compound can also be purified by column chromatography. The purification procedure can be suitably set according to the target purity.

In addition, a liquid separation procedure can be carried out following completion of the reaction by adding an aqueous alkaline solution irrespective of the precipitated state of the compound represented by general formula (1). The aqueous alkaline solution used is that in which, for example, sodium hydroxide, potassium hydroxide, sodium bicarbonate, potassium bicarbonate, sodium carbonate, potassium carbonate or the like, is dissolved in water. A suitable solvent can be added to facilitate the liquid separation procedure. Examples of the added solvent include ether-based solvents such as diethyl ether, diisopropyl ether or methyl t-butyl ether, benzene-based solvents such as benzene, toluene, xylene, mesitylene, chlorobenzene or dichlorobenzene, ester-based solvents such as ethyl acetate, isopropyl acetate or butyl acetate, hydrocarbon-based solvents such as hexane, heptane, cyclohexane or methylcyclohexane, and halogen-based solvents such as dichloromethane, dichloroethane or chloroform. The solution containing a compound represented by general formula (1) obtained in this manner can be repeatedly subjected to a liquid separation procedure using the aforementioned aqueous alkaline solution or water as necessary.

In the case of a solution in which a compound represented by general formula (1) has been extracted, the target compound represented by general formula (1) can be obtained by distilling off the solvent. Although moisture can be removed with a desiccant such as sodium sulfate or magnesium sulfate before distilling off the solvent, this operation is not essential. The compound represented by general formula (1) obtained in this manner can be purified by washing, re-precipitating or recrystallizing or by column chromatography with a suitable solvent, in the same manner as the previously described methods.

The following provides an explanation of a method for obtaining a compound represented by general formula (2) by reacting a compound represented by general formula (3) with a compound represented by general formula (4).

R1, R2, X and n in general formula (3) have the same meanings as R1, R2, X and n in general formula (1).

The compound represented by general formula (3) includes the isomers indicated below. These isomers may be present alone or a mixture of two or more types. There are no particular limitations on the mixing ratio in the case of the mixtures.

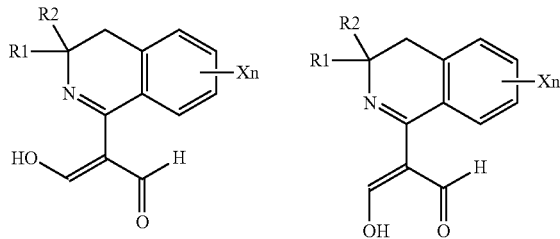

Y and m in general formula (4) have the same meanings as Y and m in general formula (1).

The compounds represented by general formula (4) can be acquired as commercial products.

There are no particular limitations on the amount of the compound represented by general formula (4) used in the reaction provided it is more than 1 equivalent based on a compound represented by general formula (3) and allows the target reaction to proceed. The amount used is preferably 1 equivalent to 3 equivalents.

Although a solvent can be used in the reaction, the use of a solvent is not necessarily required.

Although there are no particular limitations on the solvent used in the reaction provided it allows the reaction to proceed, examples thereof include ether-based solvents such as diethyl ether, diisopropyl ether or methyl t-butyl ether, alcohol-based solvents such as methanol, ethanol or isopropanol, benzene-based solvents such as benzene, toluene, xylene, mesitylene, chlorobenzene or dichlorobenzene, ester-based solvents such as ethyl acetate, isopropyl acetate or butyl acetate, nitrile-based solvents such as acetonitrile, amide-based solvents such as N-methylpyrrolidone, N,N-dimethylformamide or N,N-dimethylacetamide, urea-based solvents such as 1,3-dimethyl-2-imidazolidinone, and chlorine-based solvents such as dichloromethane, dichloroethane or chloroform. The solvent is preferably a benzene-based solvent.

Although there are no particular limitations on the amount of solvent used in the reaction provided it allows the reaction to proceed, it is normally 3 times to 50 times the weight of the compound represented by general formula (3).

Although there are no particular limitations on the temperature when carrying out the reaction provided it allows the reaction to proceed, it is normally higher than 40° C. and lower than 150° C. or the boiling point of the solvent.

With respect to moisture present in the reaction, the reaction proceeds efficiently by removing water from the reaction system. At this time, there are no particular limitations on the use of normal pressure or reduced pressure provided the reaction is allowed to proceed. The pressure may be suitably set as necessary.

The following provides a description of a method for post-treatment of the reaction.

In the case a compound represented by general formula (2) precipitates following completion of the reaction, the compound can be filtered out and isolated while in the form of a precipitate. In addition, the compound can also be used directly in the next step without isolating. Moreover, the compound can be used in the next step after having distilled off the solvent.

Although the compound represented by general formula (2) formed following completion of the reaction can be subjected to a liquid separation procedure provided the compound does not decompose, a liquid separation procedure is not essential.

The resulting compound represented by general formula (2) can be washed, re-precipitated or recrystallized with a suitable solvent. Examples of solvents used include water, ether-based solvents such as diethyl ether, diisopropyl ether or methyl t-butyl ether, alcohol-based solvents such as methanol, ethanol or isopropanol, benzene-based solvents such as benzene, toluene, xylene, mesitylene, chlorobenzene or dichlorobenzene, ester-based solvents such as ethyl acetate, isopropyl acetate or butyl acetate, hydrocarbon-based solvents such as hexane, heptane, cyclohexane or methylcyclohexane, and halogen-based solvents such as dichloromethane, dichloroethane or chloroform, and one type can be used alone or two or more types can be used by mixing at an arbitrary ratio. In addition, the compound can also be purified by column chromatography. Purification can be suitably set according to the target purity.

The compound represented by general formula (2) obtained in this manner can be converted to a compound represented by general formula (1) by a method in which it is allowed to react in the presence of an acid as previously described.

The following provides an explanation of a method for obtaining a compound represented by general formula (3) by hydrolyzing a salt containing a compound represented by general formula (5).

R1, R2, X and n in general formula (5) have the same meanings as R1, R2, X and n in general formula (1).

The alkyl group having 1 to 3 carbon atoms at R3 in general formula (5) refers to a methyl group, ethyl group, propyl group or isopropyl group, and is preferably a methyl group.

Examples of the salts containing a compound represented by general formula (5) include salts of a compound represented by general formula (5) with an anion, such as chloride ion, bromide ion, iodide ion, dichlorophosphate ion, perchlorate ion or hexafluorophosphate ion. There are no particular limitations on the type of anion provided it allows the reaction to proceed.

The compound represented by general formula (5) includes the isomers indicated below. These isomers may be present alone or a mixture of two or more types. There are no particular limitations on the mixing ratio in the case of the mixtures.

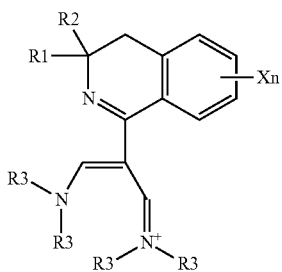

Water is required when carrying out the reaction. In addition, the reaction can be carried out using water as solvent.

There are no particular limitations on the amount of water used provided it is more than 2 equivalents based on the compound represented by general formula (5). Water is normally used in excess, and the amount used is 2 to 50 times the weight of the compound represented by general formula (5).

The pH is preferably from neutral to alkaline when carrying out the reaction. When making the pH alkaline, an inorganic base such as sodium hydroxide, potassium hydroxide, sodium bicarbonate, potassium bicarbonate, sodium carbonate or potassium carbonate can be used. The use amount thereof is suitably set so that the aqueous layer is alkaline.

A solvent can be used when carrying out the reaction. Examples of the solvents used include ether-based solvents such as diethyl ether, diisopropyl ether or methyl t-butyl ether, alcohol-based solvents such as methanol, ethanol or isopropanol, benzene-based solvents such as benzene, toluene, xylene, mesitylene, chlorobenzene or dichlorobenzene, ester-based solvents such as ethyl acetate, isopropyl acetate or butyl acetate, hydrocarbon-based solvents such as hexane, heptane, cyclohexane or methylcyclohexane, and halogen-based solvents such as dichloromethane, dichloroethane or chloroform. One type of these solvents can be used alone or two or more types can be used by mixing at an arbitrary ratio. Although there are no limitations on the reaction state provided it allows the reaction to proceed, the reaction state may be a single layer or two layers separated.

The amount of the solvent used is normally 2 times to 50 times the weight of the salt containing a compound represented by general formula (5).

The reaction temperature is normally higher than −10° C. and lower than 150° C. or the boiling point of the solvent. The reaction temperature is preferably higher than 20° C. and lower than 120° C. or the boiling point of the solvent.

The reaction can be made to proceed efficiently by removing dialkylamine ((R3)$_2$NH) formed during the reaction from the reaction system.

The pressure when carrying out the reaction may be normal pressure or the reaction can be carried out under reduced pressure so as to efficiently remove dialkylamine.

The following provides a description of a method for post-treatment of the reaction.

Following completion of the reaction, a liquid separation procedure can be carried out if the organic layer and aqueous layer are in a separated state. A solvent can also be added at this time. Examples of the added solvent include ether-based solvents such as diethyl ether, diisopropyl ether or methyl t-butyl ether, benzene-based solvents such as benzene, toluene, xylene, mesitylene, chlorobenzene or dichlorobenzene, ester-based solvents such as ethyl acetate, isopropyl acetate or butyl acetate, hydrocarbon-based solvents such as hexane, heptane, cyclohexane or methylcyclohexane, and halogen-based solvents such as dichloromethane, dichloroethane or chloroform. In addition, a liquid separation procedure can be carried out using the aforementioned added solvents even when the reaction is carried out with water alone. One type of solvent can be used alone or two or more types can be used by mixing at an arbitrary ratio. In addition, the liquid separation procedure can be repeated corresponding to the target purity.

The compound represented by general formula (3) present in a solvent obtained in this manner can be used as is without subjecting to purification, or can be used after having distilled off the solvent. Although moisture can be removed with a desiccant such as sodium sulfate or magnesium sulfate before distilling off the solvent, this operation is not essential. In addition, the compound can also be purified by washing, re-precipitating or recrystallizing using a suitable solvent if necessary. Examples of the solvents used include water, ether-based solvents such as diethyl ether, diisopropyl ether or methyl t-butyl ether, alcohol-based solvents such as methanol, ethanol or isopropanol, benzene-based solvents such as benzene, toluene, xylene, mesitylene, chlorobenzene or dichlorobenzene, ester-based solvents such as ethyl acetate, isopropyl acetate or butyl acetate, hydrocarbon-based solvents such as hexane, heptane, cyclohexane or methylcyclohexane, and halogen-based solvents such as dichloromethane, dichloroethane or chloroform, and one type of these solvents can be used alone or two or more types can be used by mixing at an arbitrary ratio. In addition, the compound can also be purified by column chromatography. Purification is suitably set according to the target purity.

The compound represented by general formula (3) obtained in the manner described above can be converted to a compound represented by general formula (1) by reacting with the aforementioned compound represented by general formula (4) to obtain a compound represented by general formula (2) and further reacting under acidic conditions.

The following provides an explanation of a method for producing a salt containing a compound represented by general formula (5) that comprises reacting a compound represented by general formula (6) with a salt containing a compound represented by general formula (7) to obtain a salt containing a compound represented by general formula (5).

R1, R2, X and n in general formula (6) have the same meanings as R1, R2, X and n in general formula (1).

The compound represented by general formula (6) can be prepared with reference to, for example, International Publication No. WO 2003/64389 or International Publication No. WO 2001/16275.

R3 in general formula (7) has the same meaning as R3 in general formula (5).

The compound represented by general formula (7) can be prepared from a formamide derivative such as N,N-dimethylformamide and a halogenating agent.

Examples of the halogenating agents used include, but are not limited to, oxalyl chloride, phosgene, phosphorous oxychloride and thionyl chloride.

The salt containing a compound represented by general formula (7) includes salts of a compound represented by general formula (7) with an anion derived from the halogenating agent. Examples of the anions derived from the halogenating agent include anions such as chloride ion and dichlorophosphate ion.

The amount of a compound represented by general formula (7) used is more than 2 equivalents based on a compound represented by general formula (6), and is preferably 2 equivalents to 5 equivalents.

A solvent can be used in the reaction. Specific examples of the solvents include benzene-based solvents such as benzene, toluene, xylene, mesitylene, chlorobenzene or dichlorobenzene, ester-based solvents such as ethyl acetate, isopropyl acetate or butyl acetate, nitrile-based solvents such as acetonitrile, amide-based solvents such as N-methylpyrrolidone, N,N-dimethylformamide or N,N-dimethylacetamide, urea-based solvents such as 1,3-dimethyl-2-imidazolidinone, and chlorine-based solvents such as dichloromethane, dichloroethane or chloroform, and one type of these solvents can be used alone or two or more types can be used by mixing at an arbitrary ratio.

Although there are no particular limitations on the amount of solvent used provided it allows the reaction to proceed, it is normally 3 times to 50 times the weight of the compound represented by general formula (6).

Although there are no particular limitations on the reaction temperature provided it allows the reaction to proceed, it is higher than −10° C. and lower than 150° C. or the boiling point of the solvent, and is preferably higher than 20° C. and lower than 120° C. or the boiling point of the solvent.

Examples of the reaction method include a procedure in which a compound represented by general formula (7) is prepared from a formamide derivative and a halogenating agent, followed by reacting with a compound represented by general formula (6), and a procedure in which a halogenating agent is allowed to react with a mixture of a compound represented by general formula (6) and a formamide derivative. There are no particular limitations on the method used provided it allows the target reaction to proceed, and the method can be set as is suitable.

The following provides a description of a method for post-treatment of the reaction.

Water can be added following completion of the reaction. A compound represented by general formula (5) is present in the aqueous layer in the case of having added a neutral or acidic aqueous solution. Alternatively, conversion to a compound represented by general formula (3) may occur in the case of having added an alkaline aqueous solution.

In the case the aqueous layer is acidic after having added water, the liquid can be separated with a solvent that is incompatible with water. Examples of the solvents used include ether-based solvents such as diethyl ether, diisopropyl ether or methyl t-butyl ether, benzene-based solvents such as benzene, toluene, xylene, mesitylene, chlorobenzene or dichlorobenzene, ester-based solvents such as ethyl acetate, isopropyl acetate or butyl acetate, hydrocarbon-based solvents such as hexane, heptane, cyclohexane or methylcyclohexane, and halogen-based solvents such as dichloromethane, dichloroethane or chloroform. A liquid separation procedure is not essential, and the reaction liquid can be transferred to the next step while still in the state of two layers.

In the case a salt of a compound represented by general formula (5) precipitates following completion of the reaction, it can be isolated by filtration. In addition, after having distilled off the solvent, it may also be isolated by adding a solvent that causes the salt to precipitate. Removal of the solvent by distillation is not essential at this time, but rather is suitably assessed based on the state of the reaction mixture. Examples of the solvents used include ether-based solvents such as diethyl ether, diisopropyl ether or methyl t-butyl ether, benzene-based solvents such as benzene, toluene, xylene, mesitylene, chlorobenzene or dichlorobenzene, ester-based solvents such as ethyl acetate, isopropyl acetate or butyl acetate, nitrile-based solvents such as acetonitrile, hydrocarbon-based solvents such as hexane, heptane, cyclohexane or methylcyclohexane, and halogen-based solvents such as dichloromethane, dichloroethane or chloroform.

The salt of a compound represented by general formula (5) can also be isolated by salt exchange with perchlorate ion or perfluorophosphate ion or the like.

In addition, the reaction of the next step can be carried out directly following completion of the reaction. In addition, it can be transferred to the next step after only carrying out removal of solvent by distillation.

The salt containing a compound represented by general formula (5) obtained in this manner can be converted to a compound represented by general formula (1) by converting to a compound represented by general formula (3) through the aforementioned hydrolysis, followed by reacting with a compound represented by general formula (4) to obtain a compound represented by general formula (2) and further reacting under acidic conditions.

The following provides a description of a method in which a compound represented by general formula (3) and a compound represented by general formula (4) are reacted in the presence of an acid to convert to a compound represented by general formula (1).

As was previously described, after obtaining a compound represented by general formula (2) by reacting a compound represented by general formula (3) with a compound represented by general formula (4), the compound represented by general formula (2) can be converted to a compound represented by general formula (1) by adding an acid. Surprisingly, by reacting with a compound represented by general formula (4) in the presence of acid in advance, a compound represented by general formula (3) can also be converted to a compound represented by general formula (1).

There are no particular limitations on the amount of the compound represented by general formula (4) used in the reaction provided it is more than 1 equivalent based on the compound represented by general formula (3) and allows the reaction to proceed. The amount used is preferably 1 equivalent to 3 equivalents, and more preferably 1 equivalent to 1.5 equivalents.

The acid used can be an inorganic acid or organic acid, and there are no particular limitations thereon provided the target reaction is allowed to proceed. Examples of the inorganic acids include hydrochloric acid, sulfuric acid and phosphoric acid, and the inorganic acid is preferably sulfuric acid or phosphoric acid. Examples of the organic acids include organic carboxylic acids and organic sulfonic acids. Examples of the organic carboxylic acids include trifluoroacetic acid and the like. Examples of the organic sulfonic acids include methanesulfonic acid, trifluoromethanesulfonic acid, benzenesulfonic acid, toluenesulfonic acid, xylenesulfonic acid, chlorobenzenesulfonic acid and naphthalenesulfonic acid. In the case the sulfonic acid has the regioisomers, any isomer is effective.

There are no particular limitations on the amount of acid used provided it is more than 1 equivalent. The amount of acid used is preferably 1 equivalent to 3 equivalents.

There are no particular limitations on the method used to charge reagents provided it allows the reaction to proceed, and it may be a method in which acid is mixed with a compound represented by general formula (4) followed by adding a compound represented by general formula (3), or a method in which a compound represented by general formula (3), a compound represented by general formula (4) and acid are mixed all at once.

Although there are no particular limitations on the solvent used in the reaction provided it allows the reaction to proceed, examples thereof include benzene-based solvents such as benzene, toluene, xylene, mesitylene, chlorobenzene or dichlorobenzene, ester-based solvents such as ethyl acetate, isopropyl acetate or butyl acetate, nitrile-based solvents such as acetonitrile, amide-based solvents such as N-methylpyrrolidone or N,N-dimethylformamide, urea-based solvents such as 1,3-dimethyl-2-imidazolidinone, and chlorine-based solvents such as dichloroethane or chloroform. The solvent is preferably a benzene-based solvent. One type of solvent can be used alone or two or more types can be used by mixing at an arbitrary ratio.

Although there are no particular limitations on the amount of solvent used in the reaction provided it allows the reaction to proceed, it is normally 3 to 50 times the weight of the compound represented by general formula (3).

Although there are no particular limitations on the reaction temperature provided it allows the reaction to proceed, it is normally higher than 40° C. and lower than 200° C. or the boiling point of the solvent.

With respect to moisture present in the reaction, the reaction proceeds efficiently by removing water from the reaction system. At this time, there are no particular limitations on the use of normal pressure or reduced pressure provided the reaction is allowed to proceed. It may be suitably set as necessary.

With respect to post-treatment following the reaction, it can be carried out using the same procedures as the methods for post-treatment explained in the method for converting a salt containing a compound represented by general formula (2) to a compound represented by general formula (1) in the presence of acid.

The compound represented by general formula (3) obtained by hydrolyzing a salt containing a compound represented by general formula (5) as previously described can be further converted to a compound represented by general formula (1) by reacting with a compound represented by general formula (4) in the presence of an acid.

The salt containing a compound represented by general formula (5) obtained by reacting a compound represented by general formula (6) with a salt containing a compound represented by general formula (7) as previously described can be converted to a compound represented by general formula (1) by hydrolyzing to convert to a compound represented by general formula (3), followed by further reacting with a compound represented by general formula (4) in the presence of an acid.

The method for producing a compound represented by general formula (2) by reacting a compound represented by general formula (3) with a compound represented by general formula (4) is a novel reaction, and the resulting compound represented by general formula (2) is also a novel compound. On the basis of the above, this novel reaction and this novel compound can be understood to be useful in the present invention.

The method for producing a compound represented by general formula (3) by hydrolyzing a salt containing a compound represented by general formula (5) is a novel reaction, and the resulting compound represented by general formula (3) is also a novel compound. On the basis of the above, this novel reaction and this novel compound can be understood to be useful in the present invention.

The method for producing a salt containing a compound represented by general formula (5) by reacting a compound represented by general formula (6) with a salt containing a compound represented by general formula (7) is novel, and the resulting salt containing a compound represented by general formula (5) is also a novel compound. On the basis of the above, this novel reaction and this novel compound can be understood to be useful in the present invention.

According to the present invention as described above, a simple and efficient method for producing 3,4-dihydroisoquinoline derivatives represented by general formula (1), and useful, novel production intermediates thereof, can be provided.

EXAMPLES

Although the following provides a more detailed explanation of the present invention by indicating examples thereof, the present invention is not limited thereto.
N,N-dimethylformamide is referred to as DMF, 1,3,3-trimethyl-3,4-dihydroisoquinoline is referred to as Compound (I),
N-(2-(3,3-dimethyl-3,4-dihydroisoquinolin-1-yl)-3-(dimethylamino)allylidene)-N-methylmethanaminium chloride is referred to as Compound (II),
2-(3,3-dimethyl-3,4-dihydroisoquinolin-1(2H)-ylidene)malonaldehyde is referred to as Compound (III),
2-(3,3-dimethyl-3,4-dihydroisoquinolin-1(2H)-ylidene)-3-(phenylimino)propanal is referred to as Compound (IV), 3-(3,3-dimethyl-3,4-dihydroisoquinolin-1-yl)quinoline is referred to as Compound (V), p-toluenesulfonic acid is referred to as TsOH, m-xylenesulfonic acid is referred to as m-XySO$_3$H, and high-performance liquid chromatography is referred to as HPLC.

Example 1

Synthesis of Compound (III) —Part 1

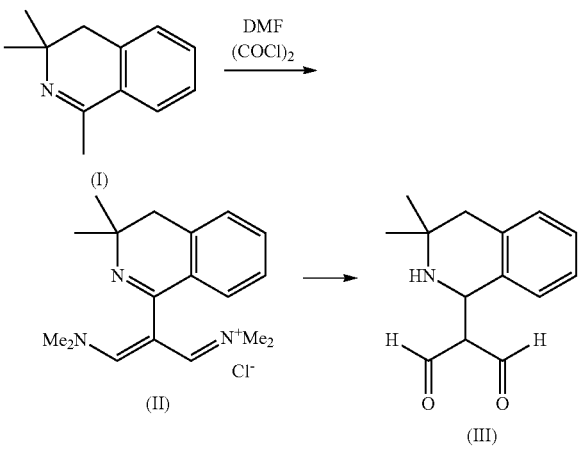

180 ml of xylene charged with 12.66 g of DMF were cooled to 4° C. followed by carefully dropping 21.98 g of oxalyl chloride at 10° C. or lower over the course of 20 minutes. After stirring for 30 minutes at room temperature (26° C.), 20 ml of xylene containing 10.00 g of Compound (I) were dropped in over the course of 10 minutes. Next, the temperature was raised to 80° C. followed by stirring for 2 hours at the same temperature. After cooling to room temperature (26° C.), adding 100 ml of water and stirring well, a xylene layer and aqueous layer were separated to obtain the aqueous layer containing Compound (II).

The resulting aqueous layer containing Compound (II) was dropped into 32.3 g of 30% sodium hydroxide and allowed to react for 2 hours at 95° C. After cooling to 8° C., 45.76 g of concentrated hydrochloric acid were dropped in at 30° C. or lower (pH≈3.5). After stirring for 1 hour, the precipitate was filtered out to obtain 10.65 g of Compound (II) as a light brown solid.

Material Data of Compound (III):

$^1$H -NMR (CDCl$_3$) δ: 12.12 (1H, br s), 9.79 (2H, s), 7.64 (1H, d, J=7.6 Hz), 7.55 (1H, t, J=7.6 Hz), 7.38 (1H, t, J=7.6 Hz), 7.29 (1H, d, J=7.6 Hz), 2.91 (2H, s), 1.32 (6H, s).

Example 2

Synthesis of Compound (IV)

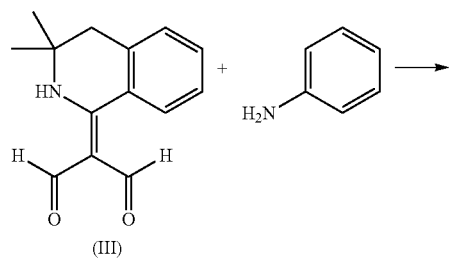

100 ml of toluene charged with 10.00 g of Compound (III) and 4.06 g of aniline were allowed to react for 10 hours while refluxing and removing water. 2.03 g of aniline were additionally added and allowed to react for 4 hours while refluxing and removing water. After cooling to room temperature, diethyl ether was added and the precipitate was filtered out. 9.41 g of Compound (IV) were obtained as a yellow solid. Yield: 71%.

Material Data of Compound (IV):

$^1$H -NMR (CDCl$_3$) δ: 13.35 (1H, br s), 9.70 (1H, s), 9.02 (1H, br s), 7.60 (1H, d, J=7.6 Hz), 7.50-7.48 (1H, m), 7.38-7.36 (3H, m), 7.29-7.28 (1H, m), 7.21-7.18 (3H, m), 2.89 (2H, s), 1.32 (6H, s).

Example 3

Synthesis of Compound (V) Using Compound (IV) as Substrate—Part 1

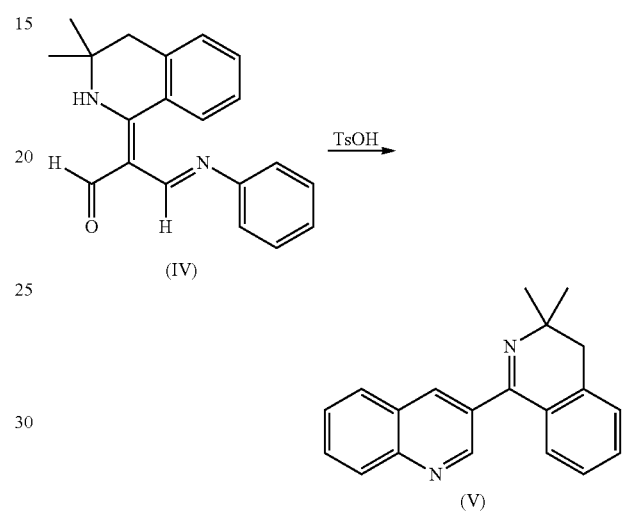

5 ml of xylene charged with 120 mg of Compound (IV) and 74 mg of p-toluenesulfonic acid monohydrate were allowed to react for 3 hours while refluxing. Following completion of the reaction, saturated aqueous sodium bicarbonate solution and ethyl acetate were added and the liquid was separated. The separated organic layer was dried by adding sodium sulfate. Next, the sodium sulfate was removed followed by distilling off the solvent under reduced pressure and purifying by column chromatography. 101 mg of the resulting compound were Compound (V). Yield: 90%. The $^1$H-NMR data of the resulting Compound (V) coincided with that described in Patent Document 1.

Example 4

Synthesis of Compound (V) Using Compound (IV) as Substrate—Part 2

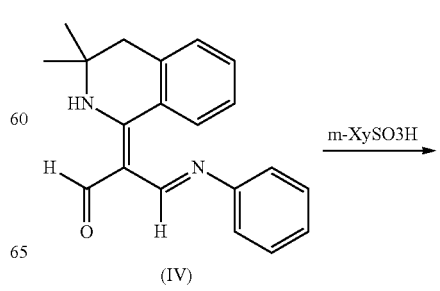

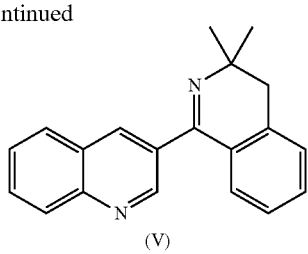

(V)

10 ml of xylene charged with 1.0 g of Compound (IV) and 0.72 g of m-xylenesulfonic acid 1.9-hydrate were allowed to react for 4 hours while refluxing. Analysis of the resulting reaction mixture by HPLC indicated that Compound (V) had been formed in a yield of 93.6%.

Example 5

Synthesis of Compound (V) Using Compound (III) as Substrate—Part 1

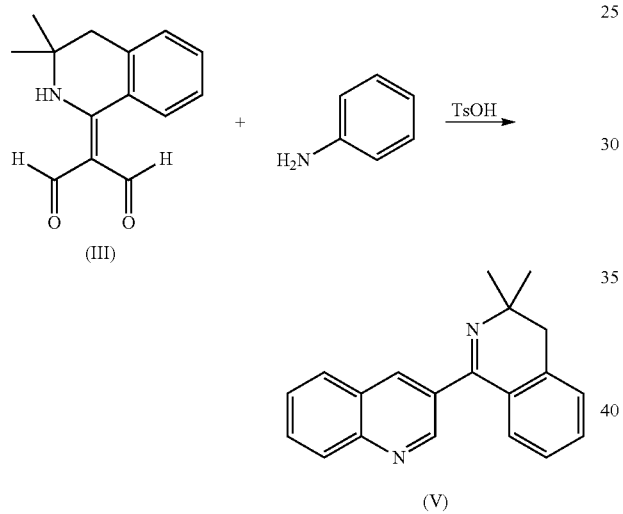

213 ml of xylene charged with 10.65 g of Compound (III) obtained in Example 1, 8.84 g of p-toluenesulfonic acid monohydrate and 4.33 g of aniline were allowed to react for 4 hours while refluxing and removing water. After cooling to room temperature, 198 g of water containing 2.04 g of sodium hydroxide and 50 ml of ethyl acetate were added followed by stirring at 50° C. Next, an organic layer and aqueous layer were separated and the organic layer was concentrated under reduced pressure to obtain 13.00 g of Compound (V) as a reddish-brown syrup having a purity of 81.1% (content: 10.54 g).

On the basis of this example, it can be understood that Compound (V) can be prepared directly from Compound (III) without isolating Compound (IV).

Example 6

Synthesis of Compound (V) Using Compound (III) as Substrate—Part 2

795 µl of aniline and 2.0 g of Compound (III) were added to a xylene solution charged with 838 mg of methanesulfonic acid, followed by reacting for 4 hours while refluxing and removing water. Analysis of the resulting reaction mixture by HPLC indicated that Compound (V) had been obtained in a yield of 89.5%.

Example 7

Synthesis of Compound (V) Using Compound (III) as Substrate—Part 3

The same reaction as Example 6 was carried out with the exception of using benzenesulfonic acid instead of methanesulfonic acid. Analysis of the resulting reaction mixture by HPLC indicated that Compound (V) had been formed in a yield of 96.4%.

Example 8

Synthesis of Compound (V) Using Compound (III) as Substrate—Part 4

The same reaction as Example 6 was carried out with the exception of using trifluoromethanesulfonic acid instead of methanesulfonic acid. Analysis of the resulting reaction mixture by HPLC indicated that Compound (V) had been formed in a yield of 82.6%.

Example 9

Synthesis of Compound (V) Using Compound (III) as Substrate—Part 5

The same reaction as Example 6 was carried out with the exception of using sulfuric acid instead of methanesulfonic acid. Analysis of the resulting reaction mixture by HPLC indicated that Compound (V) had been formed in a yield of 80.3%.

Example 10

Synthesis of Compound (V) Using Compound (III) as Substrate—Part 6

The same reaction as Example 6 was carried out with the exception of using p-chlorobenzenesulfonic acid instead of methanesulfonic acid. Analysis of the resulting reaction mixture by HPLC indicated that Compound (V) had been formed in a yield of 96.0%.

Example 11

Synthesis of Compound (V) Using Compound (III) as Substrate—Part 7

The same reaction as Example 6 was carried out with the exception of using 2-naphthalenesulfonic acid instead of methanesulfonic acid. Analysis of the resulting reaction mixture by HPLC indicated that Compound (V) had been formed in a yield of 94.1%.

Example 12

Synthesis of Compound (V) Using Compound (III) as Substrate—Part 8

The same reaction as Example 6 was carried out with the exception of using phosphoric acid instead of methanesulfonic acid. Analysis of the resulting reaction mixture by HPLC indicated that Compound (V) had been formed in a yield of 64.6%.

Example 13

Synthesis of 3-(3,3-dimethyl-3,4-dihydroisoquinolin-1-yl)-7-fluoroquinoline

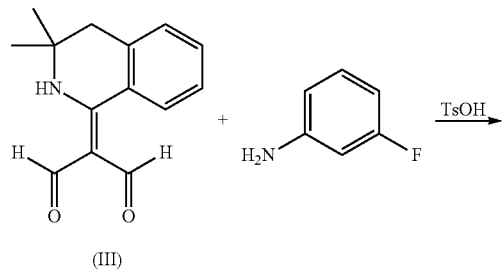

5 ml of xylene charged with 0.23 g of Compound (III), 0.19 g of p-toluenesulfonic acid monohydrate and 0.11 g of 3-fluoroaniline were allowed to react for 4.5 hours while refluxing. Following completion of the reaction, ethyl acetate and saturated sodium bicarbonate solution were added followed by separating the liquid and drying the organic layer with sodium sulfate. The sodium sulfate was removed followed by distilling off the solvent under reduced pressure and purifying the residue with a silica gel column to obtain 0.26 g of the title compound as a pale yellow solid (isolated yield: 86%).

Material Data of Title Compound:

$^1$H-NMR (CDCl$_3$) δ: 9.11 (1H, d, J=2.1 Hz), 8.38 (1H, d, J=2.1 Hz), 7.88-7.87 (1H, m), 7.79 (1H, dd, J=10.0, 2.4 Hz), 7.43-7.42 (1H, m), 7.39-7.37 (1H, m), 7.29-7.24 (2H, m), 7.19 (1H, d, J=6.9 Hz), 2.87 (2H, s), 1.33 (6H, s).

Example 14

Synthesis of 3-(3,3-dimethyl-3,4-dihydroisoquinolin-1-yl)-7-methoxyquinoline

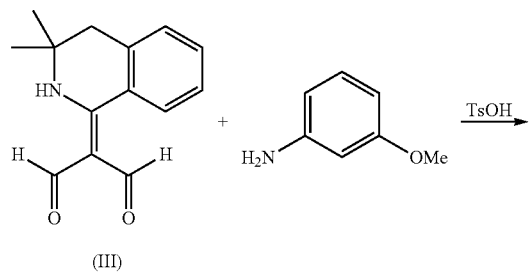

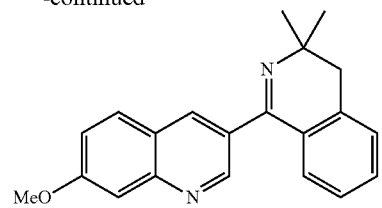

The same reaction as Example 13 was carried out with the exception of using m-anisidine instead of 3-fluoroaniline. The title compound was obtained in an isolated yield of 99%.

Material Data of Title Compound:

$^1$H-NMR (CDCl$_3$) δ: 9.03 (1H, d, J=2.1 Hz), 8.30 (1H, d, J=2.1 Hz), 7.75 (1H, d, J=8.9 Hz), 7.48 (1H, d, J=2.1 Hz), 7.42-7.41 (1H, m), 7.26-7.23 (4H, m), 3.98 (3H, s), 2.86 (2H, s), 1.32 (6H, s).

Example 15

Synthesis of 7-bromo-3-(3,3-dimethyl-3,4-dihydroisoquinolin-1-yl)quinoline

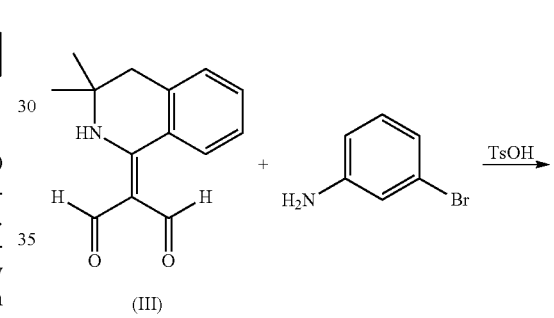

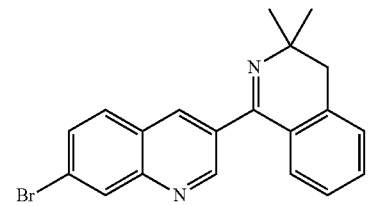

The same reaction as Example 13 was carried out with the exception of using 3-bromoaniline instead of 3-fluoroaniline. The title compound was obtained as a yellow wax in an isolated yield of 63%.

Material Data of Title Compound:

¹H -NMR (CDCl₃) δ: 9.11 (1H, d, J=2.1 Hz), 8.35 (2H, s), 7.74 (1H, d, J=8.9 Hz), 7.67 (1H, dd, J=8.9, 1.4 Hz), 7.43 (1H, t, J=7.6 Hz), 7.29-7.24 (2H, m), 7.18 (1H, d, J=7.6 Hz), 2.87 (2H, s), 1.33 (6H, s).

Example 16

Synthesis of 6-bromo-3-(3,3-dimethyl-3,4-dihydroisoquinolin-1-yl)quinoline

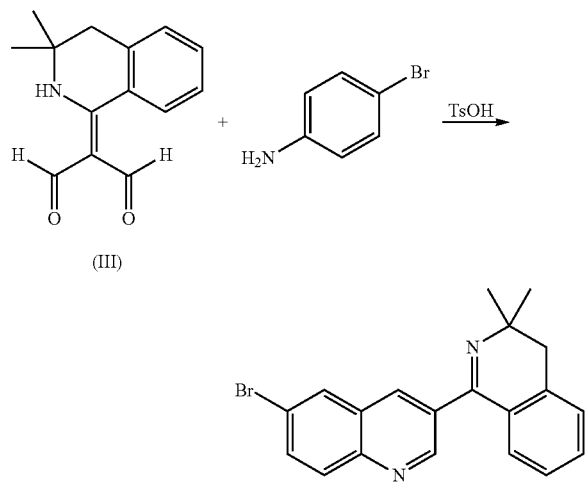

The same reaction as Example 13 was carried out with the exception of using 4-bromoaniline instead of 3-fluoroaniline and changing the reaction time from 4.5 hours to 9 hours. The title compound was obtained as a red wax in an isolated yield of 54%.

Material Data of Title Compound:

¹H -NMR (CDCl₃) δ: 9.12 (1H, d, J=2.1 Hz), 8.27 (1H, d, J=2.1 Hz), 8.03-8.02 (2H, m), 7.82 (1H, dd, J=8.9, 2.1 Hz), 7.43 (1H, td, J=7.6, 1.4 Hz), 7.29-7.23 (2H, m), 7.17 (1H, d, J=7.6 Hz), 2.87 (2H, s), 1.33 (6H, s).

Example 17

Synthesis of 3-(3,3-dimethyl-3,4-dihydroisoquinolin-1-yl)-5,7-dimethoxyquinoline

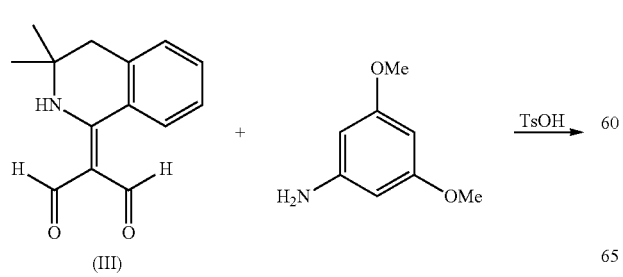

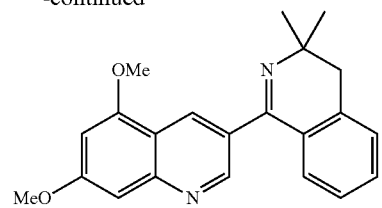

20 ml of xylene containing 1.0 g of Compound (III), 0.67 g of 3,5-dimethoxyaniline and 0.83 g of p-toluenesulfonic acid monohydrate were allowed to react for 30 minutes while refluxing. 5% aqueous sodium hydroxide solution and ethyl acetate were added followed by separating the liquid and drying the resulting organic layer with sodium sulfate. The sodium sulfate was removed followed by distilling off the solvent under reduced pressure and adding isopropyl ether to the residue and stirring. The precipitate was filtered out to obtain 1.33 g of the title compound as a white solid. Yield: 88%.

Material Data of Title Compound:

¹H -NMR (CDCl₃) δ: 9.00 (1H, d, J=2.1 Hz), 8.62 (1H, d, J=2.1 Hz), 7.42-7.40 (1H, m), 7.25-7.24 (3H, m), 7.08 (1H, d, J=2.1 Hz), 6.54 (1H, d, J=2.1 Hz), 3.97 (3H, s), 3.96 (3H, s), 2.85 (2H, s), 1.32 (6H, s).

Example 18

Synthesis of 3-(3,3-dimethyl-3,4-dihydroisoquinolin-1-yl)-6,7-dimethylquinoline

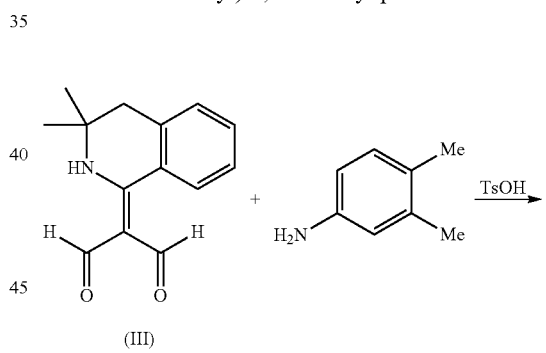

The same reaction as Example 13 was carried out with the exception of using 3,4-dimethylaniline instead of 3-fluoroaniline. The title compound was obtained as a yellow solid in an isolated yield of 96%.

Material Data of Title Compound:

¹H-NMR (CDCl₃) δ: 9.00 (1H, d, J=2.1 Hz), 8.24 (1H, d, J=2.1 Hz), 7.90 (1H, s), 7.59 (1H, s), 7.41 (1H, td, J=7.2, 1.6 Hz), 7.27-7.18 (3H, m), 2.86 (2H, s), 2.50 (3H, s), 2.46 (3H, s), 1.32 (6H, s).

Example 19

Synthesis of 3-(3,3-dimethyl-3,4-dihydroisoquinolin-1-yl)-5,7-dimethylquinoline

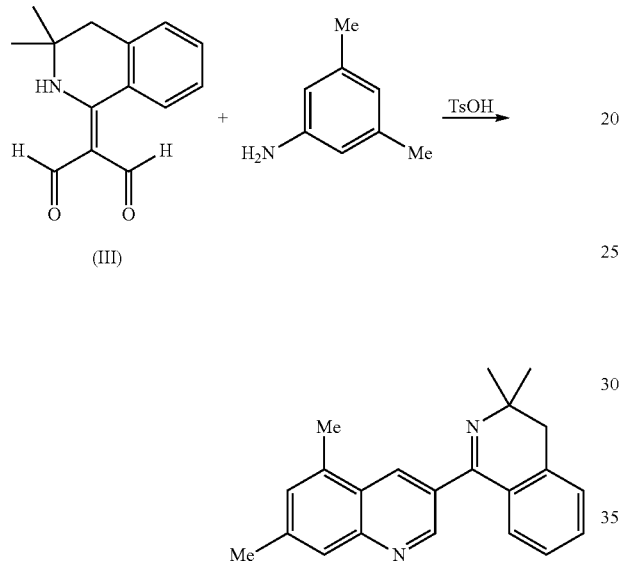

The same reaction as Example 13 was carried out with the exception of using 3,5-dimethylaniline instead of 3-fluoroaniline. The title compound was obtained as an orange oily substance in an isolated yield of 94%.

Material Data of Title Compound:

¹H-NMR (CDCl₃) δ: 9.03 (1H, d, J=2.1 Hz), 8.45 (1H, d, J=1.4 Hz), 7.78 (1H, s), 7.41 (1H, td, J=7.6, 1.4 Hz), 7.26-7.21 (4H, m), 2.87 (2H, s), 2.67 (3H, s), 2.55 (3H, s), 1.34 (6H, s).

Example 20

Synthesis of 3-(3,3-dimethyl-3,4-dihydroisoquinolin-1-yl)-8-methoxyquinoline

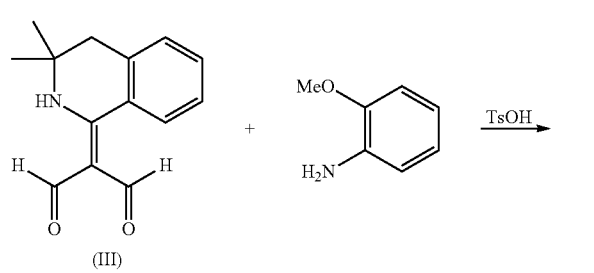

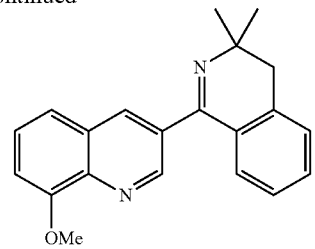

20 ml of mesitylene containing 1.0 g of Compound (III), p-toluenesulfonic acid monohydrate and 0.55 g of o-anisidine were allowed to react for 8 hours while refluxing. 18% hydrochloric acid was added followed by heating and stirring at 50° C. and separating the liquid. 10% sodium hydroxide solution and ethyl acetate were added to the resulting aqueous layer followed by separating the liquid and drying the organic layer with sodium sulfate. The sodium sulfate was removed followed by distilling off the solvent under reduced pressure and purifying the residue with a silica gel column. 0.71 g of the title compound was obtained. Yield: 51%.

Material Data of Title Compound:

¹H-NMR (CDCl₃) δ: 9.06 (1H, d, J=2.1 Hz), 8.39 (1H, d, J=2.1 Hz), 7.52-7.39 (3H, m), 7.27-7.26 (1H, m), 7.22 (1H, t, J=7.6 Hz), 7.17 (1H, d, J=7.6 Hz), 7.10 (1H, d, J=7.6 Hz), 4.12 (3H, s), 2.87 (2H, s), 1.33 (6H, s).

Example 21

Synthesis of 8-bromo-3-(3,3-dimethyl-3,4-dihydroisoquinolin-1-yl)quinoline

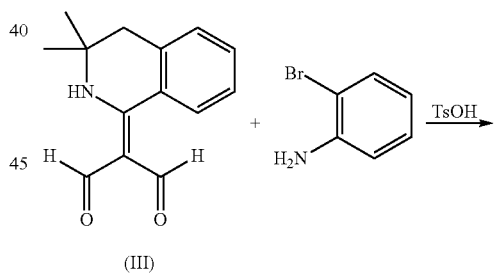

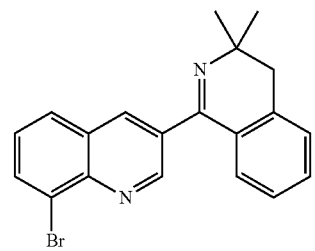

The same reaction as Example 20 was carried out with the exception of using 2-bromoaniline instead of o-anisidine. The title compound was obtained as a brown oily substance in a yield of 21%.

Material Data of Title Compound:

$^1$H-NMR (CDCl$_3$) δ: 9.20 (1H, d, J=2.1 Hz), 8.43 (1H, d, J=2.1 Hz), 8.09 (1H, dd, J=7.6, 1.4 Hz), 7.87-7.85 (1H, m), 7.44-7.43 (2H, m), 7.27-7.20 (3H, m), 2.87 (2H, s), 1.33 (6H, s).

Example 22

Synthesis of Compound (III) —Part 2

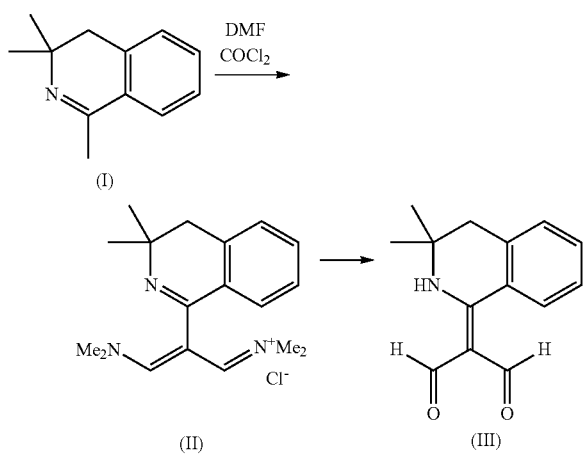

910 ml of a xylene solution containing 91.55 g of DMF were cooled to 2° C. followed by blowing 109.2 g of phosgene over the course of 30 minutes. After stirring for 30 minutes at room temperature, 140 ml of xylene containing 70.0 g of Compound (I) were added dropwise. Next, the temperature was raised to 90° C. followed by stirring for 5 hours. After cooling to 45° C., 595 ml of water were added and stirred. Analysis of the reaction mixture by HPLC indicated that 127.29 g of Compound (II) had formed (reaction yield: 98.5%).

286.52 g of water containing 71.63 g of sodium hydroxide were dropped into the aforementioned reaction mixture followed by stirring for 5 hours at 90° C. After cooling to 30° C., insoluble material was removed followed by liquid separation. Analysis of the resulting xylene layer by HPLC indicated that 82.57 g of Compound (III) were contained (reaction yield: 90.5%).

Example 23

Synthesis of Compound (II) —Part 1

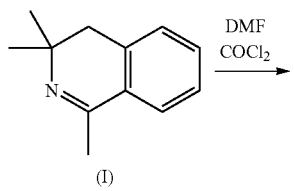

-continued

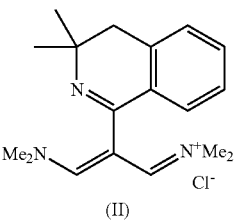

A xylene solution containing 9.99 g of phosgene was dropped into 105 ml of xylene containing 9.15 g of DMF and 7.0 g of Compound (I) over the course of 20 minutes. Next, the temperature was raised to 90° C. followed by stirring for 5 hours at the same temperature. After cooling to 45° C., 119 ml of water were added dropwise and stirred. Measurement of the resulting reaction mixture by HPLC indicated that 12.41 g of Compound (II) had formed. Reaction yield: 96.0%.

Example 24

Synthesis of Compound (II) —Part 2

The same reaction as Example 23 was carried with the exception of using butyl acetate instead of xylene. Compound (II) was formed in a reaction yield of 93.2%.

Example 25

Synthesis of 2p-toluenesulfonate Salt of Compound (V)

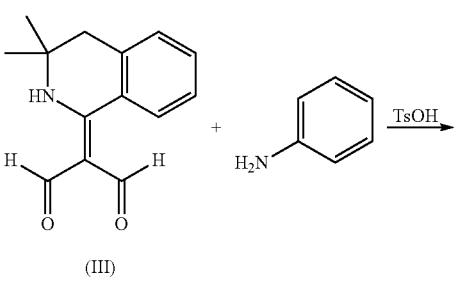

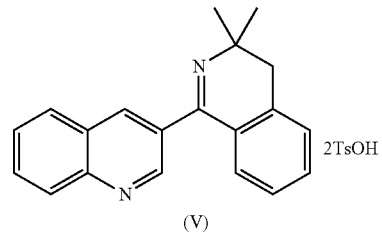

10.01 g of Compound (III), 4.28 g of aniline and 100.39 g of xylene were mixed followed by stirring for 1 hour at 140° C. A xylene solution of p-toluenesulfonic acid prepared by heating 18.38 g of p-toluenesulfonic acid monohydrate and 50.69 g of xylene to 140° C. while dehydrating was charged into this heated solution followed by stirring for 4 hours at 140° C. Following completion of the reaction, the reaction liquid was cooled to 70° C. followed by the addition of 39.35 g of isopropanol thereto and refluxing for 1 hour at 85° C. to 88° C. After cooling to room temperature, the precipitated solid was filtered out and further washed with 71.95 g of xylene. The resulting solid was dried under reduced pressure to obtain 25.78 g of the title compound as a pale yellow solid (yield: 93.6%).

Material Data of Title Compound:

Melting point: 235° C. to 236° C.

$^1$H -NMR (DMSO-d6) δppm: 1.53 (6H, s), 2.29 (6H, s), 3.35 (2H, s), 7.12 (4H, dd, J=0.6, 8.6 Hz), 7.47 (4H, dd, J=0.6, 8.6 Hz), 7.53 (1H, td, J=1.2, 8.0 Hz), 7.57 (1H, dd, J=1.2, 8.0 Hz), 7.62 (1H, d, J=7.3 Hz), 7.83 (1H, ddd, J=1.2, 6.9, 8.3 Hz), 7.89 (1H, td, J=1.2, 7.3 Hz), 8.04 (1H, ddd, J=1.2, 6.9, 8.3 Hz), 8.23 (1H, d, J=8.3 Hz), 8.25 (1H, d, J=8.3 Hz), 8.92 (1H, d, J=2.1 Hz), 9.14 (1H, d, J=2.1 Hz), 13.25 (2H, brs).

Example 26

Hexafluorophosphate Salt of Compound (II)

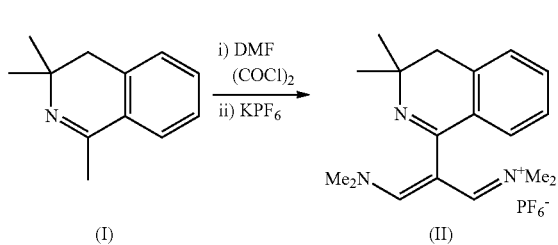

63.0 g of DMF were cooled to 5° C. followed by dropping 16.12 g of oxalyl chloride therein while keeping the temperature lower than 10° C. After stirring for 30 minutes, 10.0 g of Compound (I) were dropped therein while keeping the temperature lower than 10° C. Following completion of the dropping, the reaction mixture was heated to 70° C. and stirred for 3 hours. Analysis by HPLC at this time indicated that Compound (II) had been formed in a yield of 98.5%. The reaction liquid cooled to 30° C. and 5 mol/L of an aqueous sodium hydroxide solution (34.6 mL) were simultaneously added dropwise into an aqueous solution of potassium hexafluorophosphate (11.69 g) cooled to 5° C. while keeping the temperature lower than 10° C. The resulting precipitate was filtered out followed by drying under reduced pressure to obtain 12.60 g of a yellow solid (yield: 53.6%).

Material Data of Title Compound:

Melting point: 172° C. to 176° C.

$^1$H -NMR (CDCl$_3$) δ: 7.73 (2H, s), 7.46 (1H, td, J=7.2, 1.4 Hz), 7.41 (1H, t, J=7.2 Hz), 7.34 (1H, dd, J=7.6, 1.4 Hz), 7.24 (1H, d, J=6.9 Hz), 3.35 (6H, s), 2.85 (6H, s), 2.77 (2H, s), 1.29 (6H, s).

Example 27

Synthesis from Compound (I) to Compound (V)

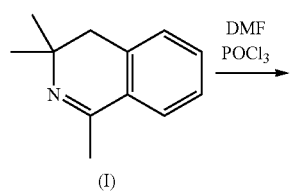

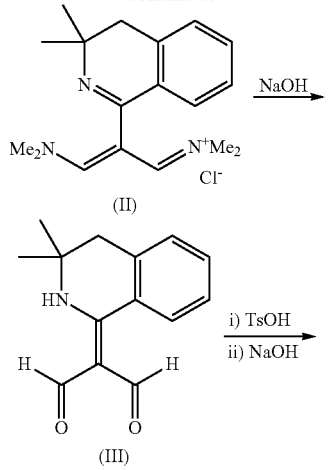

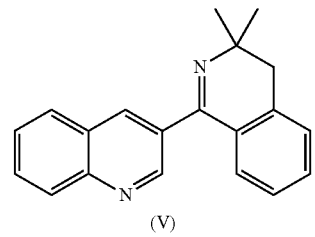

40.70 g of phosphoryl chloride were dropped into a solution cooled to 1° C. obtained by mixing 24.05 g of DMF with 223.17 g of xylene while keeping the temperature lower than 10° C. followed by stirring for 30 minutes. A mixed solution of 18.39 g of Compound (I) and 34.33 g of xylene was dropped therein followed by heating to 90° C. After stirring for 20 hours at 90° C., the reaction liquid was dropped into 240.64 g of 20% aqueous sodium hydroxide solution cooled to 2° C. Next, the temperature was raised to 60° C. under reduced pressure (160 mmHg to 200 mmHg) followed by stirring for 6 hours while removing the aqueous dimethylamine solution formed by the reaction using a Dean-Stark tube. After cooling the reaction liquid to room temperature, insoluble material was filtered out followed by liquid separation of the filtrate. Analysis of the organic layer by HPLC confirmed that Compound (III) had been formed in a reaction yield of 89.5%. 9.27 g of aniline and 40.83 g of xylene were added to the resulting organic layer followed by heating to 140° C. and stirring for 1 hour. 107.11 g of xylene charged with 39.67 g of p-toluenesulfonic acid in the uniform state by heating and stirring at 140° C. were dropped therein followed by stirring for 3 hours at the same temperature. After cooling to 85° C., 87.0 g of isopropanol were added followed by stirring for 1 hour. The solid was filtered out after cooling to 25° C. and stirring for 2 hours. The resulting solid was dried to obtain 56.48 g of 2p-toluenesulfonate salt of Compound (V) as a yellow solid (purity: 98.4%).

491.82 g of chlorobenzene and 500 g of 1.5% aqueous sodium hydroxide solution were added to 50.00 g of the 2p-toluenesulfonate salt of Compound (V) followed by stirring for 1 hour at room temperature. The organic layer obtained by a liquid separation procedure was dehydrated at 45° C. under reduced pressure to obtain 486.01 g of a chlorobenzene solution containing Compound (V). Measurement by HPLC indicated that the content of Compound (V) was 21.82 g.

Industrial Applicability

According to the present invention, 3,4-dihydroisoquinoline derivatives can be provided efficiently by a simple procedure. Moreover, the present invention has high value in terms of industrial use since it enables industrial production to be carried out advantageously.

The invention claimed is:

1. A method for producing a compound represented by formula (1):

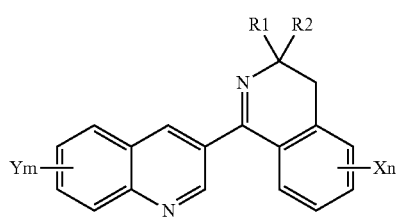

wherein R1 and R2 independently represent an optionally substituted alkyl group having 1 to 6 carbon atoms or R1 and R2 together with the carbon atom to which they are bound form an optionally substituted cycloalkyl group having 3 to 10 carbon atoms, X represents a halogen atom, optionally substituted alkyl group having 1 to 6 carbon atoms or optionally substituted alkoxy group having 1 to 6 carbon atoms, n represents an integer of 0 to 4, Y represents a halogen atom, optionally substituted alkyl group having 1 to 6 carbon atoms or optionally substituted alkoxy group having 1 to 6 carbon atoms, and m represents an integer of 0 to 4, comprising reacting a compound represented by formula (2):

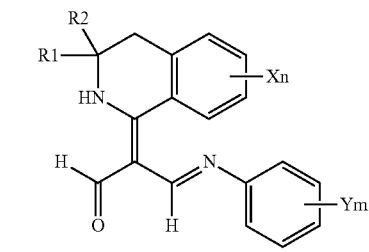

wherein R1, R2, X, Y, n and m are the same as previously defined, in the presence of an acid.

2. The method for producing a compound represented by formula (1) described in claim 1, wherein R1 and R2 independently represent an optionally substituted alkyl group having 1 to 6 carbon atoms.

3. The method for producing a compound represented by formula (1) described in claim 2, wherein n is 0.

4. The method for producing a compound represented by formula (1) described in claim 1, wherein a compound represented by formula (2) is obtained by reacting a compound represented by formula (3):

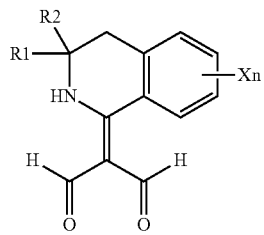

wherein R1, R2, X and n are the same as in claim 1, with a compound represented by formula (4):

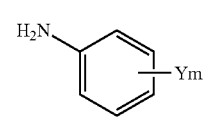

wherein Y and m are the same as in claim 1.

5. The method for producing a compound represented by formula (1) described in claim 4, wherein R1 and R2 independently represent an optionally substituted alkyl group having 1 to 6 carbon atoms.

6. The method for producing a compound represented by formula (1) described in claim 5, wherein n is 0.

7. The method for producing a compound represented by formula (1) described in claim 4, wherein a compound represented by formula (3) is obtained by hydrolyzing a salt containing a compound represented by formula (5):

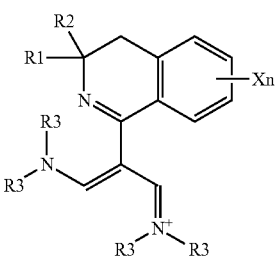

wherein R1, R2, X and n are the same as in claims 4 and R3 is an alkyl group having 1 to 3 carbon atoms.

8. The method for producing a compound represented by formula (1) described in claim 7, wherein R1 and R2 independently represent an optionally substituted alkyl group having 1 to 6 carbon atoms.

9. The method for producing a compound represented by formula (1) described in claim 8, wherein n is 0.

10. The method for producing a compound represented by formula (1) described in claim 7, wherein a salt containing a compound represented by formula (5) is obtained by reacting a compound represented by formula (6):

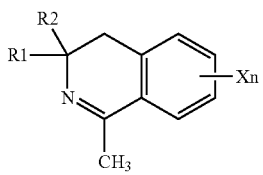
(6)

wherein R1, R2, X and n are the same as in claim 7, with a salt containing a compound represented by formula (7):

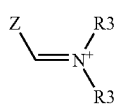
(7)

wherein R3 is the same as in claim 7 and Z represents a halogen atom.

11. The method for producing a compound represented by formula (1) described in claim 10, wherein R1 and R2 independently represent an optionally substituted alkyl group having 1 to 6 carbon atoms.

12. The method for producing a compound represented by formula (1) described in claim 11, wherein n is 0.

13. A method for producing a compound represented by formula (1):

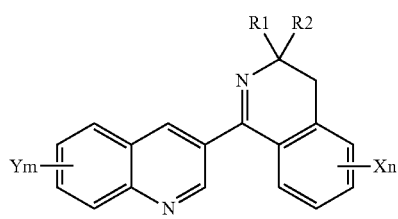
(1)

wherein R1 and R2 independently represent an optionally substituted alkyl group having 1 to 6 carbon atoms or R1 and R2 together with the carbon atom to which they are bound form an optionally substituted cycloalkyl group having 3 to 10 carbon atoms, X represents a halogen atom, optionally substituted alkyl group having 1 to 6 carbon atoms or optionally substituted alkoxy group having 1 to 6 carbon atoms, n represents an integer of 0 to 4, Y represents a halogen atom, optionally substituted alkyl group having 1 to 6 carbon atoms or optionally substituted alkoxy group having 1 to 6 carbon atoms, and m represents an integer of 0 to 4, comprising reacting a compound represented by formula (3):

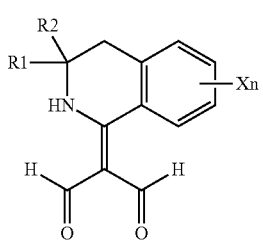
(3)

wherein R1, R2, X and n are the same as previously defined, with a compound represented by formula (4):

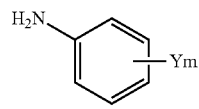
(4)

wherein Y and m are the same as previously defined, in the presence of an acid.

14. The method for producing a compound represented by formula (1) described in claim 13, wherein R1 and R2 independently represent an optionally substituted alkyl group having 1 to 6 carbon atoms.

15. The method for producing a compound represented by formula (1) described in claim 14, wherein n is 0.

16. The method for producing a compound represented by formula (1) described in claim 13, wherein a compound represented by formula (3) is obtained by hydrolyzing a salt containing a compound represented by formula (5):

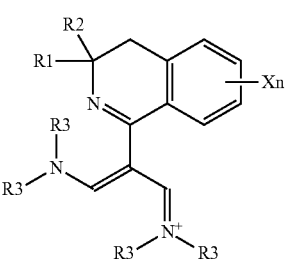
(5)

wherein R1, R2, X and n are the same as in claims 13 and R3 represents an alkyl group having 1 to 3 carbon atoms.

17. The method for producing a compound represented by formula (1) described in claim 16, wherein R1 and R2 independently represent an optionally substituted alkyl group having 1 to 6 carbon atoms.

18. The method for producing a compound represented by formula (1) described in claim 17, wherein n is 0.

19. The method for producing a compound represented by formula (1) described in claim 16, wherein a salt containing a compound represented by formula (5) is obtained by reacting a compound represented by formula (6):

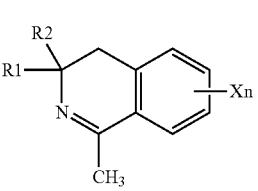
(6)

wherein R1, R2, X and n are the same as in claim 16, with a salt containing a compound represented by formula (7):

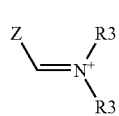 (7)
wherein R3 is the same as in claim 16 and Z represents a halogen atom.
20. The method for producing a compound represented by formula (1) described in claim 19, wherein R1 and R2 independently represent an optionally substituted alkyl group having 1 to 6 carbon atoms.
21. The method for producing a compound represented by formula (1) described in claim 20, wherein n is 0.
* * * * *